United States Patent [19]

Goldstein et al.

[11] 4,044,599
[45] Aug. 30, 1977

[54] TEST SYSTEM FOR EVALUATION OF ARMORS USING DUPLICATE FRAGMENTS

[75] Inventors: David Goldstein, Adelphi; William C. Pless, Havre de Grace; Michael Shapiro, Oxon Hill, all of Md.; Dana Spencer, Woodbridge, Va.; Leland E. Starr, Jr., Silver Spring, Md.

[73] Assignee: The United States of America as represented by the Secretary of the Navy, Washington, D.C.

[21] Appl. No.: 663,003

[22] Filed: Mar. 1, 1976

[51] Int. Cl.² ............................................. G01N 3/08
[52] U.S. Cl. ............................ 73/12; 102/27 R; 102/DIG. 2; 346/107 R
[58] Field of Search ........................... 73/12, 35, 167; 354/130, 131; 346/107 R; 102/27 R, DIG. 2

[56] References Cited

U.S. PATENT DOCUMENTS

| | | | |
|---|---|---|---|
| 2,992,087 | 7/1961 | Fassnocht et al. | 102/27 R |
| 2,999,743 | 9/1961 | Breza et al. | 102/27 R X |
| 3,154,014 | 10/1964 | Dunne | 73/12 |
| 3,204,527 | 9/1965 | Godfrey et al. | 73/12 X |
| 3,249,046 | 5/1966 | Balchan et al. | 73/12 X |
| 3,605,482 | 9/1971 | Humes | 73/12 |
| 3,625,052 | 12/1971 | Jones | 73/12 X |
| 3,771,620 | 11/1973 | Lockwood | 73/167 X |

Primary Examiner—Richard C. Queisser
Assistant Examiner—Charles Gorenstein
Attorney, Agent, or Firm—R. S. Sciascia; A. L. Branning; W. C. Anderson

[57] ABSTRACT

A test system comprises a propulsion unit for directing salvos of ballistic fragments in a planar wave to a target of test material. The fragments are stroboscopically illuminated for photographic recording of the test results.

9 Claims, 3 Drawing Figures

TEST SYSTEM FOR EVALUATION OF ARMORS USING DUPLICATE FRAGMENTS

BACKGROUND OF THE INVENTION

This invention relates to test systems, and more particularly to a testing device for evaluating armor material and ballistic fragments.

The evaluation of armor materials by using fragmenting munitions has long been difficult and expensive to perform under controlled conditions. A method traditionally used in armor testing and evaluation involved mounting a fragment simulator in a propellant casing, firing the projectile from a barrel at the test material, causing the projectile to pass through at least a pair of velocity-measuring screens, and then evaluating the resultant impact. After each individual firing, the system had to be refurnished before another fragment simulator could be launched. The use of the two screen velocity-measuring device made it mandatory that only one simulator could be launched with each firing. Thus, to evaluate any sizeable quantity of fragments and/or armor materials was extremely time consuming. Furthermore, the use of the fragment simulator, a bluntnose projectile, did not result in accurate test data truly representative of the damage behavior of actual munition fragments. In the search for test projectiles that would more closely duplicate the behavior of actual fragments, spherical, cubical and right cylindrical masses were used in place of the fragment simulators. These means, however, were not entirely satisfactory, and did not overcome the shortcomings inherent in the fragment simulator test system.

Efforts to use actual fragments resulted in the "arena" test method, wherein a munition shell was placed in the center of a circle of armor test materials, the shell detonated to spray a shower of fragments toward the circle of test material, and the armor damages evaluated. The disadvantages of this method far outnumbered the sole benefit of using actual, natural fragments. The probabilities of target impact by the fragments were haphazard and time penalties involved in this method are apparent. Since there was no way to collect, evaluate and categorize the fragments before the test, there were no means of assessing the effectiveness of the armor material against all types of fragments. Further, it was impossible to measure the velocity and mass of the fragments. Additionally, since the shell was statically detonated, the fragments did not have the initial velocity of a launched munition.

In another method involving the use of actual fragments, the fragments from an exploded munition were gathered and classified according to mass and shape. Then representative fragments were mounted in sabots and fired from gun barrels. The problems of cost, time consumption and data scatter inherent in this method are similar to those involved in the use of fragment simulations.

It is thus apparent that in the foregoing methods the use of actual fragments or fragment simulators produces data that is widely scattered, partial, or biased. Other problems are encountered in the use of actual fragments as test projectiles, including: (1) the cost and difficulty of obtaining and classifying the fragments; (2) problems with launching and maintaining the orientation of the fragments; (3) the lack of uniformity in fragment shape and size; and (4) the large scatter in fragment ballistic data. If these problems could be solved, actual fragments would be the test projectiles preferred over any fragment simulator or fragment model.

Closer equivalence to expected field performance of armor materials could be obtained if it were possible to project duplicate fragments against the material under consideration. Factory production of duplicates of actual fragments would result in uniformity of fragment shape and size, and the cost of production and variety of fragments could be closely controlled, thus resolving two of the foregoing problems associated with use of actual fragments. By analyzing the fragments from actual shells or other fragmenting munitions, it is possible to determine representative fragments or series of fragments from a particular shell or fragmenting munition. Selected fragments may then be reproduced by a suitable process, such as cold forging or precision molding. The mass and the area presented, or the ratio of these quantities (mass-to-area-presented, M.A.P.) can be closely controlled, so that in combination with the proper explosive the fragment velocity can be carefully monitored.

Use of an explosive producing a planar shock wave, such as a sheet explosive, as the propulsion system will result in fragment orientation very nearly that of the actual munition fragments without requiring the use of a launch barrel, considerably simplifying the launch problem. This simplification permits the test firing of a large number of fragments, which is a simple resolution of the large scatter in fragment ballistic data.

As with any testing procedure or apparatus, some permanent record of the test results must be made for later evaluation and analysis. The velocities and fragment quantities involved in armor materials testing compound the problem of recording the test results. Use of an accurately-timed, stroboscopic illumination source of precise duration and a still camera permits recording of the fragment trajectories on a sngle piece of film.

SUMMARY OF THE INVENTION

Accordingly, it is an object of this invention to provide a test system for the evaluation of armor materials.

Another object of the invention is to provide a test system for the evaluation of armor materials using duplicates of actual fragments as test projectiles.

Another object of the invention is to provide an armor material test system which mitigates the cost and difficulty of obtaining and classifying projectile fragments associated with the use of actual fragments.

Yet another object of the invention is to provide an armor material test system which mitigates the problems of launching test projectile fragments so as to closely resemble an actual, fragmenting munition.

Still another object of the invention is to provide an armor material test system which maintains accurate launch orientation of the test projectile fragments without requiring the use of a launch barrel.

Still another object of the invention is to provide an armor material test system using duplicates of natural fragments having controlled shape and mass.

A further object of the invention is to provide an armor material test system which will provide more reliable ballistic fragment data.

A still further object of the invention is to provide a test system for the evaluation of ballistic projectiles.

Yet a further object of the invention is to provide a test system for evaluating armor materials and ballistic projectiles having accurate means of producing a permanent record of the test results.

Briefly, these and other objects of the invention are attained in a test system comprising a test projectile propulsion means, a target of test material, and a recording apparatus including a camera and a stroboscopically-controlled illumination source. A layer of ballistic fragments is attached to the propelling charge to be directed at the target in a planar wave without use of a launch barrel. Stroboscopic illumination of precise duration permits test recordings of high fragment velocities with minimum image blur.

BRIEF DESCRIPTION OF THE DRAWINGS

A more complete understanding of the invention and a fuller appreciation of the many attendant advantages thereof will be derived by reference to the following detailed description when considered in connection with the accompanying drawings wherein.

DESCRIPTION OF THE PREFERRED EMBODIMENTS

Figure 1:
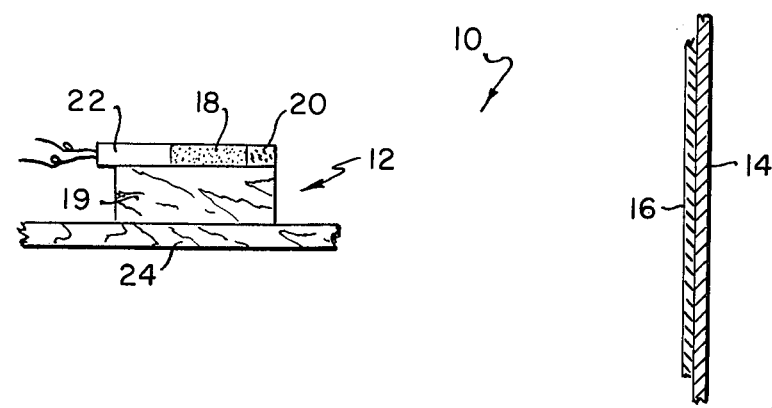
FIG. 1 is a schematic of the test system.

Referring now to the drawings wherein like reference characters designate identical or corresponding parts throughout the several views, and more particularly to FIG. 1 thereof, the test system 10 comprises a fragment propulsion unit 12 and a target 14, supporting a piece of material 16 to be tested, such as a piece of armor material. Propulsion unit 12 includes a propelling charge 18 attached to and supported by a mounting block 19. Attached to the propelling charge 18, on the surface directed toward the target 14, is a layer of fragments 20. A detonator 22 is suitably attached to the propelling charge for remote initiation thereof by means known in the art. The propulsion unit 12 rests upon a support 24, which is movable to permit variation of the distance and the angular orientation between the fragments and the target. Alternatively, the target 14 may be suitably supported to permit distance and angular adjustments relative to the propulsion unit 12. Of course, both the target and the propulsion unit can both be movable supported for the greatest flexibility in adjustments.

Launching of the fragments in a planar wave provides a predictable launch pattern without requiring the use of a launch barrel to guide the projectiles, and permits fragment orientation so that the fragments strike the target in a predictable pattern and with a uniform velocity. In flight the fragments assume a natural orientation. Any of a number of compositions or combination of compositions may be selected as the fragment propelling charge 18, provided a resultant planar shock wave is generated to impart the same initial velocity to each fragment in the layer 20 at the same instant. Since the shock waves are propogated as circles in the plane of the propelling charge, or as cylinders through the thickness of the charge, with the point of detonation, i.e., the detonator 22, as the center, the requirement of a planar shock wave can be satisfied by positioning the fragment layer 20 sufficiently far from the detonator 22 such that the curvature of the shock wave is relatively insignificant. This position will, of course, be dependent upon the type of propelling charge material used. A convenient rule-of-thumb would be a ratio of five-to-one for the ratio of the distance between the detonator and the fragment layer to the width of the fragment layer, as measured parallel to the test target 14. Positioning of the fragment layer too close to the detonator results in a spherical flow of fragments, rather than the desired collimated, or planar, flow. The spherical fragment flow produces excessive spread of the fragments, thus resulting in widely-scattered impact with the target.

The propelling charge material 18 should be selected primarily for its characteristic as a propellant, rather than as an explosive. The brisance of an explosive-type material may be too high, resulting in a shock loading of the fragment layer 20 and subsequent shattering of the test fragments. A number of these propelling charge materials are available commercially, of which Octal is an example, a composition comprising cyclotetramethylene-tetranitramine (HMX) and trinitrotoluene (TNT). Two ratios of HMX and TNT which are expecially useful are 70:30 and 75:25. Other material such as Barytol and pentolite are also suitable. Selection of different propelling charge material is one means of changing the velocity with which the fragments strike the target.

A paticularly convenient form of propelling charge material is sheet explosives, one of which is available from E. I. duPont under the name of EL 506C (or Detasheet) and fulfills the requirements of Military Specification MIL-E-46676A(MU). In using a sheet explosive material with the test system as shown in FIG. 1, the material is cut into a triangular or tapered shape, supported upon the block 19 so that a rectangular surface faces the target 14, and is suitably secured, as by taping. The apex of the taper is directed away from the target (to the left in FIG. 1) and is attached to a suitable detonator, such as the E-99 available from E. I. duPont. The tapered shape of the sheet explosive permits detonation at a single point, and a uniform progression of the detonation front produces a planar shock wave.

The projectile fragments 20 are attached to the surface of the propelling charge 18 in a layer by any appropriate means, such as with tape or with adhesive compatible with the propelling charge, or just by embedding the fragments into the propelling charge surface. The fragments directed at the target in any given salvo may be of the same species to assess the effectiveness of the fragment type or the effectiveness of the armor material to a particular type of fragments, or the fragment species may be mixed to simulate the fragment mix produced by a fragmenting munition. Fragments used with the test system 10 are preferably duplicate of natural fragments, as indicated hereinabove. Any suitable process may be used to produce these duplicate fragments. For example, the duplicates may be cold forged or cast. A particularly suitable forging technique known in the art utilizes a plurality of individually supported and adjustable die faces which are brought together to from the volume of the duplicate fragment. The use of individual die faces permits greater accuracy in reproducing the intricate surfaces of the fragments and a greater flexibility in the variety of fragments produced.

Figure 2:
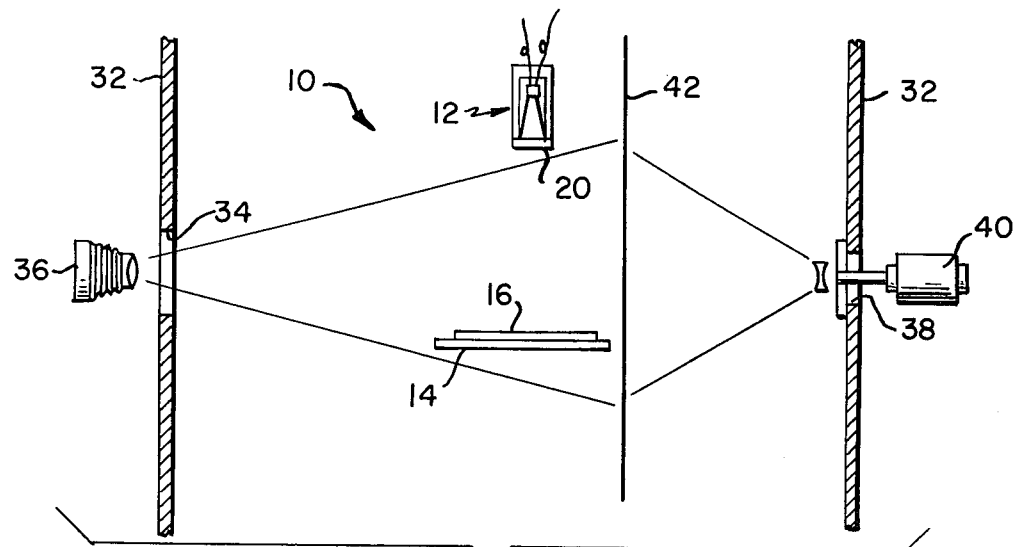
FIG. 2 is a schematic of the test system using a laser, back lighting arrangement for recording test results.

Due to the quantity of fragment projectiles propelled by the unit 12 and the fragment velocities involved, it is necessary that a photographic means be used to record the test. By using stroboscopically-controlled illumination, the high-speed flight of the fragments can be captured on one photograph. Shown schematically in FIG. 2 is an example arrangement of the test system 10 using a back lighting source. The test system 10, including the propulsion unit 12 and the test target 14, are positioned within a safety enclosure defined by the shielding partitions 32. An opening 34 is provided in one of the partitions 32 through which a camera 36 is focused on the test system 10. Another opening 38 in an opposite partition is provided to permit passage of illumination from a source 40. By way of illustration only, the source 40 may be a laser or any other illumination means that can be stroboscopically controlled, with the flash duration and the interval between flashes being adjustably regulated. Hereinafter, FIGS. 2 and 3 will be considered with a laser as the example illumination source 40, it being understood that any other suitable illumination may be used. Radiation from the laser 40 illuminates the target 14 and the fragments from the side after passing through a translucent screen 42. The screen 42, of any suitable material, e.g., frosted glass, plastic etc., is movably supported to permit relative position adjustments between the test system 10 and the laser 40, and serves to absorb excess laser radiation to prevent overexposure of the film in the camera 36. The openings 34 and 38 may be covered with any suitable, transparent material to further increase the protection offered by the partitions 32.

Figure 3:
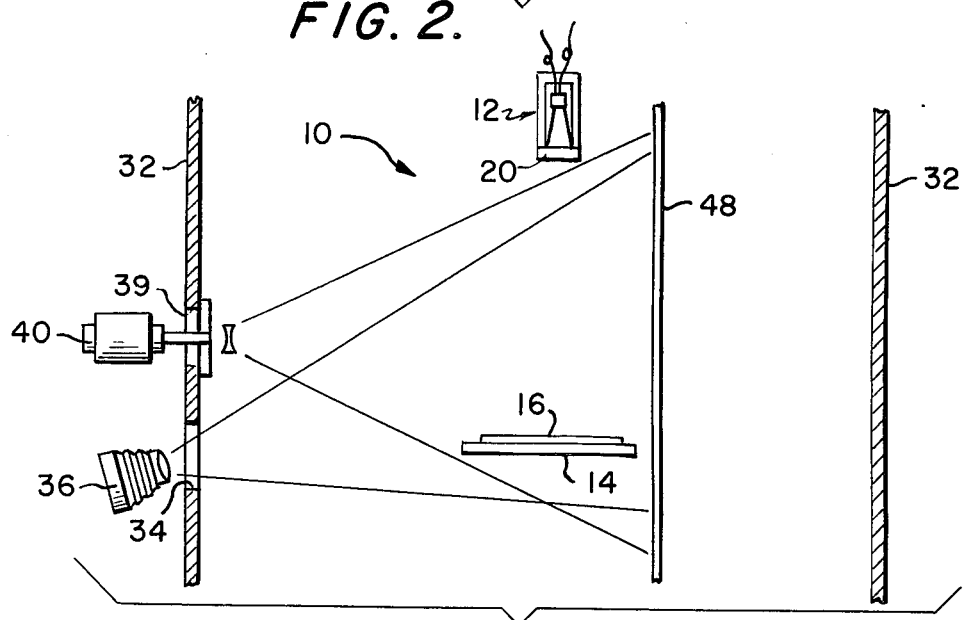
FIG. 3 is a schematic of the test system using a laser, front lighting arrangement for recording test results.

The example arrangement in FIG. 3 permits illumination of the test target from the front, i.e., from the same side as the camera. As in FIG. 2, the test system 10 is positioned within a protective safety enclosure defined by the shielding partitions 32. In this arrangement, both the camera 36 and the laser 40 are focused through the openings 34 and 39 in one of the partitions 32. The beam from the laser 40 is focused across the flight path of the fragment projectiles. Positioned behind the test system 10 is a black, background panel 48 which absorbs the radiation not striking the projectiles to prevent laser flash and overexposed film.

The laser source 40 in the above test system arrangements are double flashed at a predetermined interval prior to projectile-target impact and directly after impact. Flash durations of approximately 20 nanoseconds have been found to limit the recorded projectile image blur to less than 0.5 mil. The time interval between the flashes can be adjusted to accommodate fragment velocities up to 6000 feet per second, with individual piece velocity obtained by film data reduction as known in the art. The resulting film record will provide a double-exposed negative showing each particle in two positions within the limits of the camera view, giving velocity, fragment attitude and fragment tumbling should there be a change in attitude between the two film exposures.

Means for controlling the activation of the detonator 22 and the flash duration and time interval between flashes of the laser 40 are known to those skilled in the art. An example of a laser pulse control means applicable to the present invention is described in the U.S. Pat. to A. M. Erickson, No. 3,660,777.

Obviously, many modifications and variations of the present invention are possible in light of the above teachings. It is therefore to be understood that, within the scope of the appended claims, the invention may be practiced otherwise than as specifically described.

What is claimed as new and desired to be secured by Letters Patent of the United States is:

1. A test system for evaluating material comprising:
    a projectile propulsion unit;
    a plurality of fragments propelled by said propulsion unit as a layer;
    a target for receiving the fragments;
    a stroboscopic light source means for periodic illumination of the test system and the fragments in flight;
    a photographic means responsive to said light source to record the test results;
    said projectile propulsion unit comprising a propelling charge producing a plane shock wave without the use of a launch barrel for the propulsion of said fragments in a layer; and
    ignition means to initiate detonation of said propelling charge.

2. The test system of claim 1 wherein said plurality of fragments are attached to the surface of said propelling charge.

3. The test system of claim 2 wherein said target comprises an armor material to be impacted by said fragments.

4. The test system of claim 2 wherein said propelling charge comprises a sheet explosive and said plurality of fragments are attached to a surface of said sheet explosive.

5. The test system of claim 4 wherein said plurality of fragments are duplicates of actual munition fragments.

6. A method of testing armor material comprising the steps of:
    assembling a plurality of fragment projectiles;
    propelling said plurality of fragment projectiles at the target of test material in a plane shock wave without the use of a launch barrel;
    stroboscopically illuminating said fragment projectiles in flight; and
    photographically recording said fragments in flight.

7. The method of claim 6 wherein the tep of propelling the plurality of fragment projectiles includes the detonation of a propelling charge producing a planar shock wave.

8. The method of claim 7 wherein the step of assembling said plurality of fragment projectiles includes the assembly of duplicates of actual munition fragments.

9. The method of claim 8 wherein the step of propelling the plurality of fragment projectiles includes the detonation of a sheet explosive having attached to a surface thereof a layer of duplicate fragment projectiles.

* * * * *